United States Patent [19]
McLeod et al.

[11] 4,259,870
[45] Apr. 7, 1981

[54] DOPPLER METHOD OF MEASURING FLOW

[75] Inventors: Francis McLeod; Spencer Silverstein, both of Ithaca; Robert J. Kurtz, New York, all of N.Y.

[73] Assignee: Howmedica Inc., New York, N.Y.

[21] Appl. No.: 15,404

[22] Filed: Feb. 26, 1979

Related U.S. Application Data

[63] Continuation-in-part of Ser. No. 685,902, May 12, 1976, Pat. No. 4,142,412.

[51] Int. Cl.³ .............................................. G01F 1/66
[52] U.S. Cl. ................................. 73/861.25; 128/663
[58] Field of Search ....................... 73/194 A; 128/663

[56] References Cited

U.S. PATENT DOCUMENTS

| 2,770,795 | 11/1956 | Peterson | 73/194 A |
| 3,028,752 | 4/1962 | Bacon | |
| 3,685,348 | 8/1972 | Bottcher et al. | |
| 3,703,652 | 11/1972 | Noda | |
| 3,766,517 | 10/1973 | Fahrbach | 73/194 A X |
| 3,783,967 | 1/1974 | Apgar | |
| 3,977,247 | 8/1976 | Hassler | 73/194 A |
| 3,987,673 | 10/1976 | Hansen | 73/194 A |
| 4,067,236 | 1/1978 | Hottinger | 73/194 A |

FOREIGN PATENT DOCUMENTS 447511 8/1972 Australia .
2285618 4/1976 France .

Primary Examiner—Charles A. Ruehl
Attorney, Agent, or Firm—Larson, Taylor and Hinds

[57] ABSTRACT

A method of determining the volume flow of a fluid through a conduit usable with a single crystal, whereby at least one of the fluid and the conduit have energy-scattering interfaces. The method in one embodiment includes transmitting a known, uniform sound field through the fluid which illuminates the entire cross-sectional area of the conduit, obtaining the Doppler signal from the received signal such that the sampling region is normal to the direction of propagation of the sound field; and obtaining the integral of the power over this surface. A known volume of fluid totally within the conduit is then sampled for the reference power return therefrom and this reference power return is divided into the first moment of the power to produce a signal proportional to the volume flow of the fluid through the conduit.

13 Claims, 6 Drawing Figures

DOPPLER METHOD OF MEASURING FLOW

CROSS-REFERENCE TO RELATED APPLICATION

This application is a continuation-in-part of a copending application Ser. No. 685,902, filed May 12, 1976, now U.S. Pat. No. 4,142,412.

FIELD OF THE INVENTION

This invention relates generally to methods for measuring the flow of energy scattering interfaces within a fluid inside a conduit and more particularly to ultrasonic pulse Doppler methods for measuring blood flow in a patient's circulatory system.

DESCRIPTION OF THE PRIOR ART

Ultrasonic Doppler flowmeters for measuring the flow of particulate-containing fluid in a conduit are well known. Examples of such devices adapted for measurement of blood flow in a patient's circulatory system are described in U.S. Pat. Nos. 3,430,625 (McLeod); 3,888,238 (Meindl et al); 3,901,077 (McCarty et al); 3,554,030 (Peronneau); 3,542,014 (Peronneau); 3,827,115 (Bom); and 3,766,517 (Fahrbach). As disclosed in these references, the flowmeter usually includes a catheter for insertion into a blood vessel of the patient.

A disadvantage of these and other prior art devices is that the accuracy of the velocity and lumen cross-sectional area measurements obtained is dependent on the orientation of the catheter with respect to the blood flow axis. All of these previous designs require a fixed orientation or position to measure the size of the lumen or the velocity.

A further disadvantage of the prior art is that either separate, specialized function transducer arrangements are required to measure both velocity and lumen area or sensitive and difficult-to-implement measurement techniques must be used in order to measure velocity and lumen area with a single, dualpurpose transducer arrangement.

A further disadvantage of the prior art catheters is their complexity and the consequent difficulty in their manufacture, necessitated by the prior methods.

BACKGROUND OF THE INVENTION

Another approach to accomplish the unambiguous measurement of blood volume flow is described in an Article by Hottinger and Meindl entitled "An Ultrasonic Technique for Unambiguous Measurement of Blood Volume Flow" published in 1974 and given at the IEEE Ultrasonic Symposium Proceedings and in the U.S. Pat. to Hottinger No. 4,067,236, both incorporated herein by reference. These references disclose a flow measurement technique that provides for multiplication of a velocity component perpendicular to a sample plane by the cross-sectional area of the sample plane. Three methods based on this principle are disclosed and in all three cases, uniform isonofication of the sample cross-section is required and must be used to measure the velocity component normal to the cross-section. The projected or effective cross-sectional area is measured by one of three methods: (1) a two-dimensional array Doppler C-scan; (2) a linear array Doppler B-scan; and (3) measurement of area in terms of Doppler signal power. The third method utilizes an inner transducer to compensate for attenuation losses and scattering losses of an annular outer transducer. A signal from a sample region which lies totally within the vessel is obtained by the inner transducer. This sample region lies totally within the region sampled by the combination of the outer and inner transducers. The projected lumen area is a ratio of signal powers from the two transducers. Unfortunately, this method requires knowledge of the sample dimensions of the inner transducer and the relative gains of the two transducers and their associated circuitry. This third method appears to be very similar to that disclosed in the U.S. Pat. to Hassler No. 3,977,247, incorporated herein by reference. This third method has further disadvantages in that the circuitry is more complicated (and hence more expensive) since two transducers and two separate electrical systems for processing the information are required. In addition, because two separate electrical systems are used, the systems must be electrically matched so that the same signal will be identically processed by both systems in order to eliminate induced errors, or the gain coefficients of each system must be known so that additional compensation circuitry can be employed.

In addition to the foregoing United States Patents mentioned hereinabove, two other patents showing similar systems and methods are depicted in U.S. Pats. to Shaw, No. 3,498,290 and to Hansen No. 3,987,673. All of these references are incorporated herein by reference to show, at least, the conventional methods and circuitry to accomplish those methods.

SUMMARY OF THE INVENTION

These and other disadvantages of the prior art are overcome by the method of the present invention. The present method is independent of the orientation and position for the measurement of volume flow.

One embodiment of the invention comprises a method for measuring the volume flow of a fluid flowing in a conduit wherein at least one of the fluid and the conduit has energy-scattering interfaces. The method comprises producing and transmitting a defined ultrasonic sound field, the sound field illuminating the entire cross-sectional area of the conduit and selecting the emission pulse length and sampling period of the received signal such that the received signal is from a sampled region normal to the direction of propagation of the transmitted sound field and then a Doppler signal is obtained from the received signal. A known volume of the fluid which lies totally within the conduit is sampled and the power return of a Doppler signal is obtained from the signal received from the known volume in order to obtain a calibrating factor. The first moment of the Doppler signal received from the normal sampled region is calculated and is then divided by the calibration factor in order to obtain the volume flow through the conduit.

In an alternative embodiment, the sound transducer is incorporated into a catheter and the method further comprises inserting the catheter into the conduit before irradiating the conduit with a known, uniform sound field produced by a pulsed, ultrasonic sound signal emitted from the transducer. The volume flow of the fluid could then be calculated as stated hereinabove.

Other objectives, features and advantages of the present invention are discussed in or are apparent from the description of the preferred embodiment of the invention found hereinbelow.

DESCRIPTION OF THE PREFERRED EMBODIMENT

Figure 1:
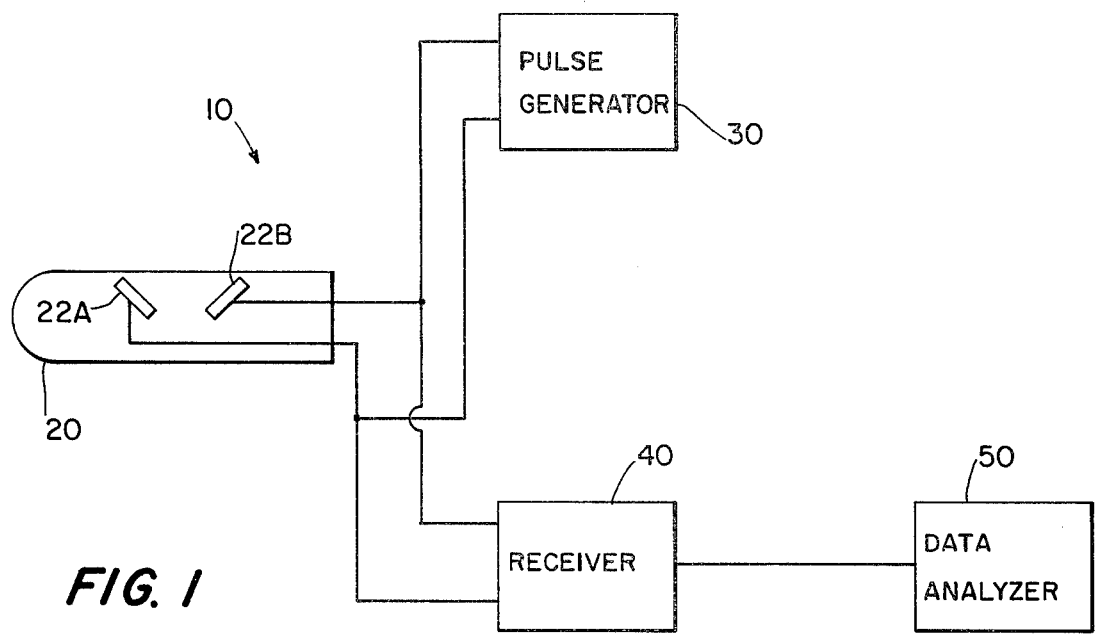
FIG. 1 is a block diagram of a flowmeter constructed according to the present invention and having two transducers incorporated in a catheter.

The mathematical starting point for determining flow is the Doppler shift vector equation. This equation is as follows:

$$f = \frac{f_o \overline{V} \cdot (\hat{T} - \hat{R})}{C}$$

f = the change in frequency
$f_o$ = the base frequency
$\overline{V}$ = Vector velocity of the fluid
C = Velocity of sound in that media
$\hat{T}$ = unit vector representing the direction of the transmitted sound beam
$\hat{R}$ = Unit vector representing the direction of the received sound beam
$(\hat{T}-\hat{R})$ = Direction Vector of observed Doppler beam The volume flow through any conduit is the vector dot product of the average velocity vector and a cross-sectional area through which that velocity flows. The present method and apparatus employ techniques for velocity measurement and cross-sectional area determinations which are independent of the orientation and position of the transducers. In order to eliminate the orientation of the transducers from being a factor in the determination of the flow velocity, in one embodiment of the invention disclosed and described in the parent application and incorporated herein by reference, two sound beams are used. However, in one of the embodiments claimed in the present application a known or defined sound beam is transmitted by a single transmitter such as by the transducers described and depicted in the figures in the parent application and incorporated into this application by reference. Each transducer (or transducers) receives signals from the entire cross-section of the conduit. A range gate is moved out in time from the transducers in order to measure a selected region of the conduit. Range gating is a commonly used timing technique for establishing regions at fixed distances (fixed time delays following the transmission of a pulse of energy) from the transducer.

Conventional apparatus and techniques for transmitting and receiving pulsed sound waves and obtaining pulsed Doppler signals on the one hand, and for using the range-gate technique to selectively provide measurements in a plurality of regions in a conduit, on the other hand, are disclosed for example in the aforementioned Peronneau U.S. Pat. No. 3,554,030 and Hottinger U.S. Pat. No. 4,067,236; and in the following articles, Hottinger and Meindl, "An Ultrasonic Technique for Unambiguous Measurement of Blood Volume Flow"; 174 Ultrasonic Symposium Proceedings, IEEE Cat. No. 74 CHO 896-ISU (Hottinger et al article); and in McLeod, "Multichannel Doppler Techniques", published as Chapter 7 of the Proceedings of the International Symposium on Ultrasonics, Janssen, Beerse, Belgium (1973), respectively.

Alternatively, the signal received can be processed either sequentially with a single movable gate or in parallel with multiple gates or in combinations thereof. Each measurement is the representation of the average velocity through that sampled region. Furthermore, the received signal, whether it is gated to be from a restricted range or from a large range interval, can be converted into a spectrum of Doppler frequencies, the average of which is a measure of the average velocity of the scatterers in the $\hat{T} - \hat{R}$ direction. When transmission and reception are by the same transducer, then the direction of $\hat{T} - \hat{R}$ is the direction of transmission.

All of the discrete range-gated velocity measurements are summed into an average velocity measurement by the use of a weighting function. This weighting function is calculated to take into account the radar equation, that is to account for transducer radiation pattern, attenuation losses, and the scattering characteristics of the reflective interface. Conventional apparatus and techniques for calculating the velocity from a received range-gated pulse Doppler signal are disclosed for example in the aforementioned Peronneau ('030) and McLeod patents and in an article by Jorgensen, Campan, Baker, "Physical Characteristics and Mathematical Modelling of the Pulsed Ultrasonic Flowmeter", July 1973 Medical and Biological Engineering 404 (Jorgensen article), the Jorgensen article also disclosing the conventional use of a weighting function to sum the velocity measurements into an average velocity measurement. The rate of scan of the transducer must be sufficiently fast so that no appreciable change in velocity takes place during the measurement period.

The next step in the measurement of flow is to measure an effective diameter or cross-sectional area. One method employs the power returned from a Doppler signal. This power is directly proportional to the size of the sampled volume. If the total sampled region over which this measurement takes place is greater than the cross-sectional area of the conduit and includes the conduit in question, the total uncalibrated cross-sectional area would be determined. This measurement can be done as a single measurement or as a sum of separate measurements. A conventional apparatus and technique for performing a power measurement are disclosed for example in the Hottinger et al article. The uncalibrated area is a function of the probe angle to the conduit wall. This uncalibrated area would also vary with different ultrasonic transducers. To obtain the effective cross-sectional area of the conduit, the uncalibrated area must be calibrated and this can be done by the following method. The power returned from a known region completely within the conduit is measured. In the preferred embodiment this is accomplished by using close-in range-gating techniques. This technique simultaneously allows the calibration of each individual transducer for gain and gives the power reflected for a known region of the fluid. Dividing this new factor into the uncalibrated power area mentioned above gives the *effective cross-sectional area*.

The effective velocity vector and the effective surface area need not necessarily be orthogonal to each other. If they are not orthogonal, the angle between the two vectors must be known so that the dot product can be determined.

Since the effective cross-sectional area is known and calibrated orthogonal to the transducers in the preferred embodiment and the effective velocity vector is known parallel to the axis of the transducers, the flow in the conduit is the product of these factors without any other factors having to be known or calibrated.

A second method for determining the cross-sectional area is to range to the wall by the use of multiple sets of transducers. Conventional apparatus and techniques for ranging the wall are disclosed in both the aforementioned Peronneau patents. In these cases, the low frequency Doppler signals, as returned from the wall, can be used to determine the wall position. A surface plane of known dimensions can be constructed from these vectors. Conventional apparatus and techniques for construction of a surface plane orthogonal to the radiation pattern are disclosed in the aforementioned Meindl et al patent. Once this effective cross-sectional area is known then this area can be multiplied by the effective velocity vector to give the volume flow through the conduit. A sufficient number of sets of transducers must be used to sample the wall if it is desired to account for any significant irregularities, and for the distance to the wall from the sets of transducers. Construction of one or more planes can now be made from the sets of transducers. The angle that the beams were transmitted and received on are known from the geometry of the probes. Since the wall has been sufficiently illuminated, the vessel shape, position of the catheter and the cross-section can all be determined by known algebraic and geometric techniques, such as taught for example in the aforementioned Peronneau patents.

A phased array is a multiple set of transducers generating or operating within a fixed time relationship to simulate a complex transducer, lens, reflector or field. Conventional apparatus and techniques for generating and using a phased array are disclosed in the aforesaid Bom patent. Once the field has been produced, the techniques for measuring the effective velocity, cross-sectional area and calibrations are as previously described.

Figure 2:
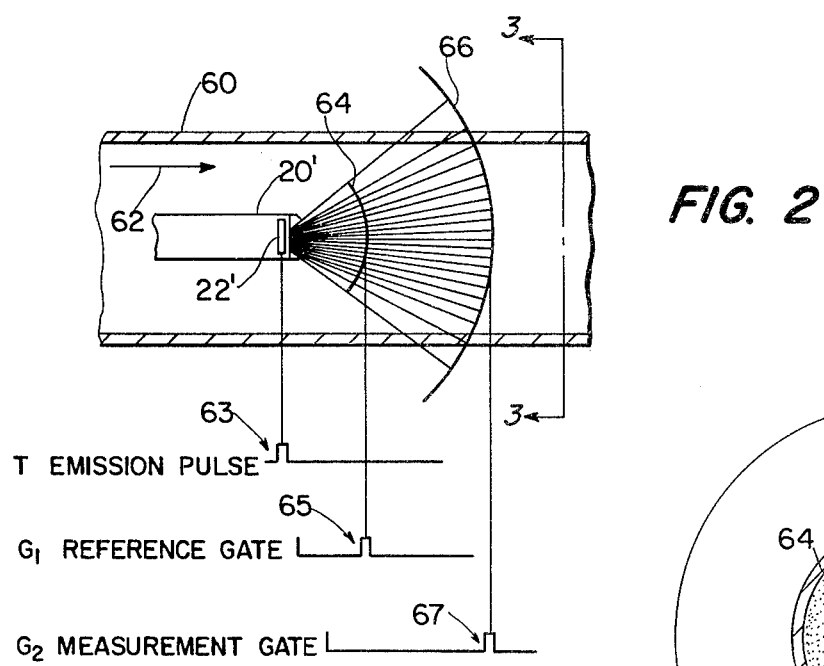
FIG. 2 is a side elevational view of a diagrammatic representation of a catheter having a single transducer and depicting a ray diagram of a transmitted sound pulse.
Figure 3:
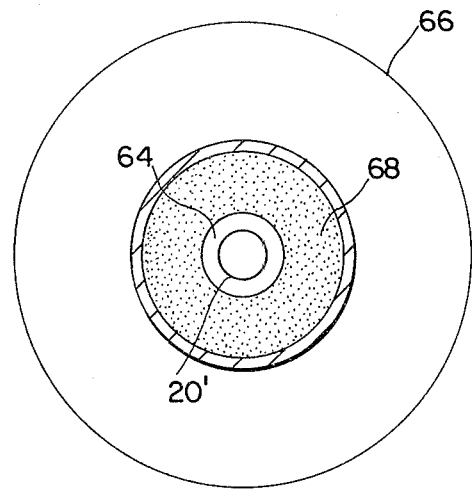
FIG. 3 is a front elevational view of the diagrammatic representation depicted in FIG. 2 and taken along line 3—3 therein.

A preferred embodiment to incorporate the transducer in a catheter or probe 20 is depicted in FIGS. 1, 2 and 3. It is to be noted that the methods described herein do not require that one of the exemplary transducer arrangements be utilized. The only requirement for the sound field is that the direction vectors must not be parallel. The direction vector is defined as the vector quantity $(\hat{T}-\hat{R})$.

Obviously, the aforementioned concepts can all be adapted extra-luminally. Arrays of two or more transmitters and one or more receivers or two or more receivers and one or more transmitters can be used.

The single transducer case involves producing a *known* uniform ultrasonic field to illuminate the total cross-section of the conduit. Conventional apparatus and techniques for generating and using a known uniform ultrasonic field are disclosed for example in the aforesaid Meindl et al patent and Hottinger patent, and the Hottinger et al article. Since the field pattern is defined, velocity measurements can be obtained. The pulse length and sampling period are selected to produce a sampling region normal to the direction of propagation of the sound beam. Under these conditions, the measured velocity component is everywhere normal to the sampling surface. The Doppler signal power returned from this surface yields a signal, the first moment of which is proportional to the flow. Conventional apparatus and techniques for calculating the integral and the moment are disclosed for example in the Hottinger et al article and in the aforesaid Hottinger patent. Calibration is provided by the same technique as previously described. As disclosed herein, the "single transducer case" refers to the generation of one sound beam and not necessarily to only one crystal transmitter/receiver. Obviously, a phased array of transducers employs more than one transducer, but only a single sound beam is generated from all of the transducers operating together in a timed relationship.

For purposes of illustration, an embodiment of a flowmeter constructed according to the present invention which is adapted for measuring blood flow in a patient's circulatory system using an intravenous catheter in the preferred embodiment will now be described.

Referring to FIG. 1, the flowmeter, which is generally denoted 10, comprises a catheter 20 having disposed therein first and second transducers, denoted 22A and 22B and referred to collectively as transducers 22, for transmitting and receiving ultrasonic sound waves; generator 30 for pulsing transducers 22; receiver 40 for receiving the signals produced by transducers 22; and data analyzer 50 for determining the blood flow velocity and an effective cross-sectional area of the vessel lumen in the region of measurement.

The sound wave pattern eminating from a single crystal transducer embodiment of the present invention is depicted in FIGS. 2 and 3. Catheter 20' having a single crystal transducer 22' is depicted inside a conduit such as a blood vessel 60. For exemplary purposes, catheter 20' is depicted in the center of blood vessel 60 and axially aligned therewith, and the blood flow is shown in the direction of arrow 62. Obviously, the orientation of catheter 20' with respect to blood vessel 60 and with respect to the blood flow is not relevant and the present invention is not dependant thereon. A known beam pattern at the measurement of a reference surface 64 enclosing a known volume located totally within blood vessel 60 and a sampling region 66 is diagrammatically shown in FIG. 2 together with the spacial location of the corresponding sound pulses or range gates on a time line or continuum for the emission pulse at 63, for the reference gate at 65, and for the measurement gate at 67. The effective cross section as discussed hereinabove is depicted at 68.

Figure 4:
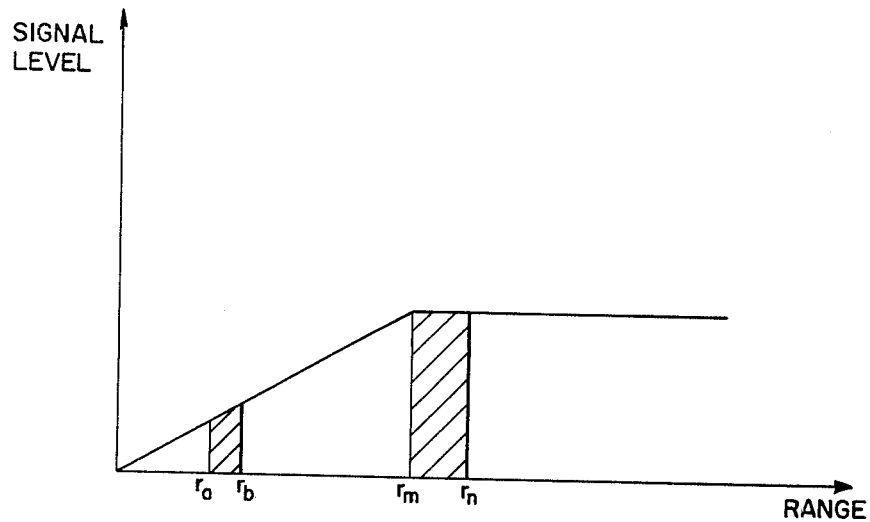
FIG. 4 is a diagrammatic graphical representation of the signal power level at various radii from the transducer.

The single transducer method, mentioned above, might be considered as a special case of the aforementioned more general multiple transducer measurement where one of the transducers was arranged to produce a beam about its own axis. The resulting range gated signal varies with the range as shown in FIG. 4. The received signal level increases with range from a distance beginning at zero at the edge of the transducer to "r", the distance to the conduit wall along the outer edge of the expanding beam pattern as the diverging beam includes more scatterers. At the distance "r", the conduit is filled and no further increase is noted. The curve is a measure of the beam area within the conduit and when multiplied by a constant yields the area on a plane perpendicular to the axis of the transducers. The effective cross-sectional area for "r" can be found by comparing the area under the curve from $r_a$ to $r_b$ where the cross-sectional area of the beam is known (beam divergence angle $\Theta$ and the distance from the transducer $r = (ct/2)$ where c = speed of sound in the medium and t = time from emission of beam to its receipt) to the curve at $r_n$ which is the area that is sought to be known.

By obtaining the power density spectrum of the received power in the range greater than $r_m$, the average value of the velocity can be obtained as the average frequency of the spectrum multiplied by a calibration constant as in the more general case discussed above. A second beam is not required in the single crystal case because the measured velocity is everywhere perpendicular to the measured cross-sectional area.

Figure 6:
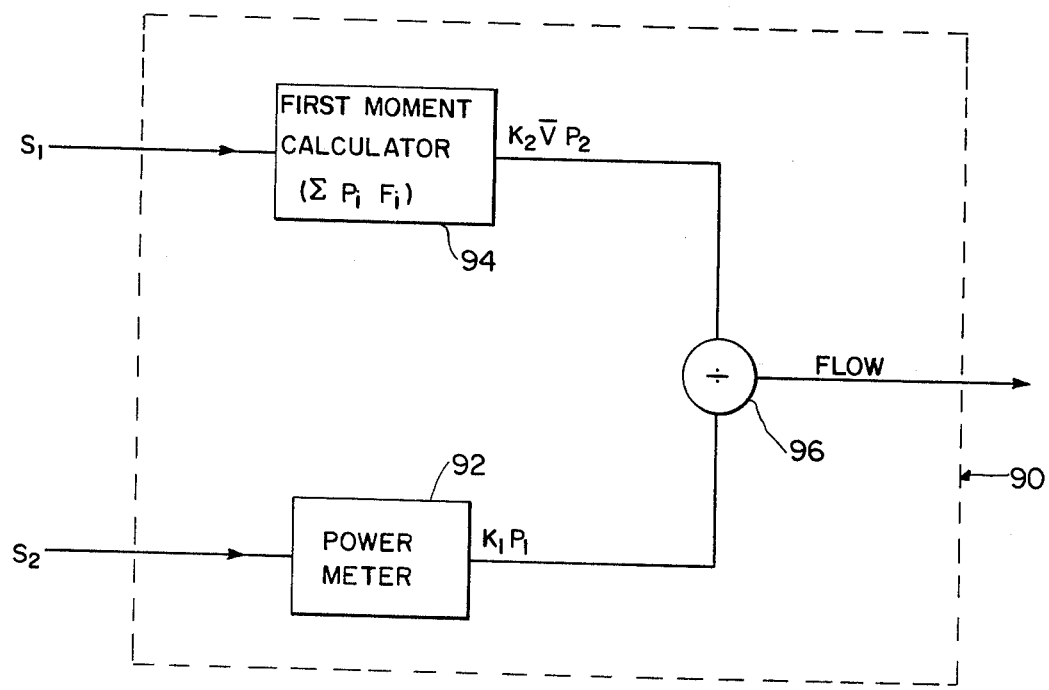
FIG. 6 is an electrical schematic block diagram of the flow processor depicted in FIG. 5.
Figure 5:
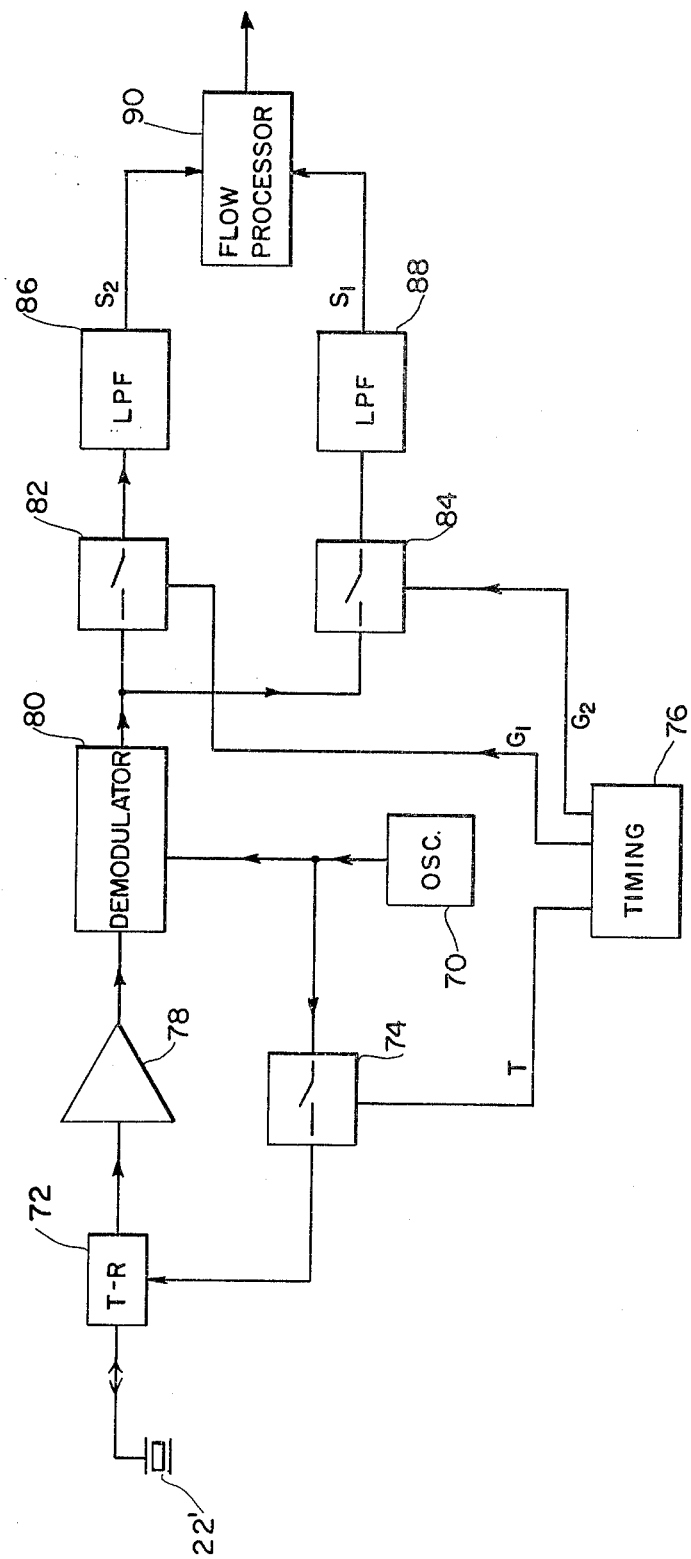
FIG. 5 is an electrical schematic block diagram of the present invention.

With reference now to FIGS. 5 and 6, there is depicted an electrical block diagram of a circuit comprised of conventional components which can carry out the method of the present invention using a single crystal. An oscillator 70 produces a reference frequency electrical signal that is sent to crystal 22' through a transmitter-receiver switch 72 and a pulse shaping switch 74 controlled by a pulse signal T (see also FIG. 2) from a timing circuit 76. Transmitter-receiver switch 72 is a conventional switch means that alternately connects crystal 22' to the transmitting circuit or to the receiving circuit. The receiving circuit is comprised of an amplifier 78 connected to a demodulator 80 which also receives as an input the reference frequency signal from oscillator 70. The output from demodulator 80 is the Doppler signal which is coupled to two parallel gating switches 82 and 84 operated by pulses $G_1$ and $G_2$ from timing circuit 76 (again refer to FIG. 2). Switch 82 is used to range gate the return signal to obtain information from a reference surface (such as surface 64) and switch 84 is used to range gate the return signal to obtain information from a measurement surface (such as surface 66). The outputs from both switches 82 and 84 are connected through respective low pass filters 86 and 88 to a flow processor 90. Low pass filters 86 and 88 are used for the conventional purpose of removing the effect of discrete samples resulting from the use of timing pulses pursuant to the sampling theorem.

A functional block diagram of flow processor 90 is depicted in FIG. 6. The output of filter 86, a signal $S_2$, is fed to a conventional power meter or wattmeter 92. The output of filter 88, signal $S_1$, is fed to a calculator 94 for calculating the first moment of the signal. The output of calculator 94, which is preferably an analog calculator, is a signal that is proportional to the average velocity of the fluid flow times the power of the returned Doppler signal from the sampling region 66, is divided in a divider 96 by the output from power meter 92. As should be apparent, the output from divider 96 is a signal that is proportional to the volume flow of the fluid.

It is to be noted that the methods to be described hereinbelow do not require that one of the exemplary transducer arrangements described in the parent application and incorporated herein by reference be utilized.

Although the invention has been described in detail with respect to exemplary embodiments thereof, it will be understood by those of ordinary skill in the art that variations and modifications may be effected within the scope and spirit of the invention.

We claim:

1. A method for determining the volume flow of a fluid flowing through a conduit by use of a single transmitting transducer, the fluid having energy-scattering interfaces, the method comprising the steps of:

producing and transmitting a defined ultrasonic pulsed sound field with a single transmitting transducer, said sound field illuminating an entire cross-section of the conduit;

receiving with a receiver means a reflected signal resulting from said transmitted sound field;

selecting the pulse length and sampling period of the received signal such that a signal is obtained from a sampled region normal to the direction of propagation of the transmitted sound field;

obtaining a Doppler signal from said received signal;

sampling a known volume of the fluid totally within the conduit with said single transducer and receiver means and obtaining the power return of a Doppler signal from the signal received from said known volume to obtain a calibrating factor;

calculating the first moment of the Doppler signal received from said normal sampled region; and dividing said first moment by said calibration factor and thereby obtaining the volume flow through the conduit.

2. A method as claimed in claim 1 wherein said transducer is located in said conduit.

3. A method as claimed in claim 1 wherein said selecting step and said sampling step use the same said received reflected signal, but use different range gates to obtain the signal from said sampled region and from said known volume.

4. A method as claimed in claim 1 wherein said sampling step comprises sampling a known volume of fluid by range gating said received signal.

5. A method as claimed in claim 1 wherein said transducer is mounted in a catheter probe which is inserted inside said conduit and wherein said pulsed sound field is transmitted in a plane perpendicular to the axis of said probe.

6. A method as claimed in claim 1 wherein the receiving step includes receiving said reflected signal with said single transducer and supplying said received reflected signal to said receiving means.

7. A method for determining the volume flow of a fluid flowing through a conduit by use of an ultrasonic transmitter/receiver means, the fluid having energy-scattering interfaces, the method comprising the steps of:

producing and transmitting a defined ultrasonic pulsed sound field with the transmitter/receiver means, said sound field illuminating an entire cross-section of the conduit;

receiving with the transmitter/receiver means a reflected signal resulting from said transmitted sound field;

selecting the pulse length and sampling period of the received signal such that a signal is obtained from a first sampled region normal to the direction of propagation of the transmitted sound field;

obtaining a Doppler signal from said received signal;

sampling a second, separate region of the fluid totally within the conduit but outside of said first sampled region with the transmitter/receiver means and obtaining the power return of a Doppler signal from the signal received from said second region to obtain a calibrating factor;

calculating the first moment of the Doppler signal received from said first sampled region; and dividing said first moment by said calibration factor and thereby obtaining a signal proportional to the volume flow through the conduit.

8. A method as claimed in claim 6 wherein said producing and transmitting step further includes producing and transmitting said sound field with a single transducer;

and wherein said receiving step further includes receiving said reflected signal with said single transducer.

9. Doppler flow apparatus for determining the volume flow of a fluid having energy-scattering interfaces and flowing through a conduit, said apparatus comprising:

a single transducer capable upon activation of generating a defined ultrasonic pulsed sound field;

means coupled to said transducer for activating said transducer to produce and transmit said sound field;

receiver means for receiving a reflected signal resulting from said transmitted sound field;

selecting means coupled to said receiver means for selecting a pulse length and sampling period of the received signal;

Doppler means coupled to said receiver means for obtaining a Doppler signal from said received signal;

calculating means coupled to said Doppler means for calculating the first moment of a received signal from a sampled region normal to the direction of propagation of the transmitted sound field;

calibration means coupled to said Doppler means for obtaining the power return of a reflected signal received from a known volume of the fluid totally within the conduit for providing a calibration factor; and means coupled to said calculating means and said calibration means for combining said calibration factor and said first moment so as to obtain the volume flow through the conduit.

10. Doppler flow apparatus as claimed in claim 9 and further including a transducer probe for containing said single transducer, said probe being insertable into the conduit.

11. Doppler flow apparatus as claimed in claim 9 wherein said receiver means includes said transducer for receiving said reflected signal.

12. Doppler flow apparatus as claimed in claim 11 wherein said calculating means and said calibration means are coupled to said Doppler means through said selecting means.

13. Doppler flow apparatus as claimed in claim 9 wherein said calculating means and said calibration means are coupled to said Doppler means through said selecting means.

* * * * *